(12) United States Patent
Annapragada et al.

(10) Patent No.: US 8,357,351 B2
(45) Date of Patent: Jan. 22, 2013

(54) NANO-SCALE CONTRAST AGENTS AND METHODS OF USE

(76) Inventors: Ananth Annapragada, Manvel, TX (US); Efstathios Karathanasis, Atlanta, GA (US); Ravi V. Bellamkonda, Marietta, GA (US); Russell M. Lebovitz, Houston, TX (US)

(*) Notice: Subject to any disclaimer, the term of this patent is extended or adjusted under 35 U.S.C. 154(b) by 557 days.

(21) Appl. No.: 12/357,950

(22) Filed: Jan. 22, 2009

(65) Prior Publication Data
US 2009/0263326 A1    Oct. 22, 2009

Related U.S. Application Data

(63) Continuation-in-part of application No. 11/595,808, filed on Nov. 10, 2006, now Pat. No. 7,785,568, and a continuation-in-part of application No. 11/568,936, filed on Dec. 27, 2007, said application No. 11/595,808 is a continuation-in-part of application No. 10/830,190, filed on Apr. 21, 2004, now Pat. No. 7,713,517, said application No. 11/568,936 is a continuation-in-part of application No. 10/830,190, filed on Apr. 21, 2004, now Pat. No. 7,713,517.

(51) Int. Cl.
*A61K 49/04* (2006.01)
*A61K 49/00* (2006.01)

(52) U.S. Cl. .......................... 424/9.1; 424/9.4
(58) Field of Classification Search .................. 424/9.4
See application file for complete search history.

(56) References Cited

U.S. PATENT DOCUMENTS

| | | | |
|---|---|---|---|
| 4,744,989 A | 5/1988 | Payne et al. | |
| 4,994,213 A | 2/1991 | Aitcheson et al. | |
| 5,049,389 A | 9/1991 | Radhakrishnan | |
| 5,094,854 A | 3/1992 | Ogawa et al. | |
| 5,204,085 A * | 4/1993 | VanDeripe | 424/9.42 |
| 5,230,882 A | 7/1993 | Unger | |
| 5,271,928 A | 12/1993 | Schneider et al. | |
| 5,312,615 A | 5/1994 | Schneider et al. | |
| 5,676,928 A | 10/1997 | Klaveness et al. | |
| 5,811,581 A | 9/1998 | Piva et al. | |
| 5,869,023 A | 2/1999 | Ericcson et al. | |
| 6,033,645 A | 3/2000 | Unger et al. | |
| 6,217,849 B1 | 4/2001 | Tournier et al. | |
| 6,425,864 B1 | 7/2002 | Foo et al. | |
| 6,468,505 B1 * | 10/2002 | Lang et al. | 424/9.321 |
| 6,475,515 B2 | 11/2002 | Sachse et al. | |
| 6,818,213 B1 * | 11/2004 | Thorpe et al. | 424/130.1 |
| 6,884,407 B1 | 4/2005 | Unger | |
| 7,033,574 B1 | 4/2006 | Schneider et al. | |
| 7,138,136 B2 | 11/2006 | Annapragada et al. | |
| 7,713,517 B2 | 5/2010 | Annapragada et al. | |
| 7,785,568 B2 | 8/2010 | Annapragada et al. | |
| 2002/0071843 A1 * | 6/2002 | Li et al. | 424/155.1 |
| 2002/0102293 A1 | 8/2002 | Sachse et al. | |
| 2002/0106328 A1 | 8/2002 | Johnson et al. | |
| 2005/0238584 A1 | 10/2005 | Annapragada et al. | |
| 2006/0235296 A1 | 10/2006 | Mattiuzzi et al. | |
| 2007/0212303 A1 | 9/2007 | Annapragada et al. | |
| 2008/0131369 A1 | 6/2008 | Annapragada et al. | |
| 2008/0206131 A1 | 8/2008 | Jaffray et al. | |
| 2008/0213350 A1 | 9/2008 | Ko et al. | |
| 2009/0263326 A1 | 10/2009 | Karathanasis et al. | |
| 2009/0311191 A1 | 12/2009 | Annapragada et al. | |
| 2010/0202974 A1 | 8/2010 | Annapragada et al. | |
| 2012/0003159 A1 | 1/2012 | Annapragada et al. | |

FOREIGN PATENT DOCUMENTS

| | | |
|---|---|---|
| EP | 0414806 | 7/1994 |
| EP | 1121102 | 8/2001 |
| WO | 88/09165 A1 | 12/1988 |
| WO | 89/11272 A1 | 11/1989 |
| WO | 95/26205 A1 | 10/1995 |
| WO | 9805364 | 2/1998 |

OTHER PUBLICATIONS

Kao, et al., Long-Residence-Time Nano-Scale Liposomal Iohexol for X-Ray-Based Blood Pool Imaging, Academic Radiology, May 2003, pp. 475-483.
Leike JU, Sachse A, Rupp K: Characterization of Continuously Extruded Iopromide-Carrying Liposomes for Computed Tomography Blood-Pool Imaging, Invest Radiol 2001; 36(6):303-8.
Torchilin, V.P, Narula, J, Halpern E, AN Khaw, B, Biochim, Biophys. Acta 1279 (1996) pp. 75-83.
Vera DR, Mattrey RF: A Molecular CT Blood Pool Contest Agent, Acad Radiol 2002; 9(7):784-92.
Sachse A., Leike JU, Schneider T , Wagner SE, Rossling, GL, Krause W , Brandl M.: Biodistribution and Computed Tomography Blood-Pool Imaging Properties of Polyethylene Glycol-Coated Iopromide-Carrying Liposomes, Invest Radiol., Jan. 1997; 32(1); 44-50.
Srinath, P. and P.V. Diwan: Stealth Liposomes—an Overview, Indian J. of Pharmacology 1994, v. 26, pp. 179-184.
Torchilin, V.P., PEG-Based Micelles as Carriers of Contrast Agents for Different Imaging Modalilities, Advanced Drug Delivery Reviews, 2002, v. 54, pp. 235-252.
Written Opinion and search report from related PCT Application No, PCT/US05/00876, Apr. 7, 2003.
Written Opinion and search report from related PCT Application No. PCT/US08/13651, Feb. 11, 2009.
Written Opinion and search report from related PCT Application No. PCT/US09/31701, May 12, 2009.
Burke et al., "Imaging of pulmonary embolism and t-PA therapy effects using MDCT and liposomal iohexol blood pool agent: preliminary results in a rabbit model." Academic Radiol., vol. 14 No. 3 p. 355-362, Mar. 2007, p. 4 para 4-6, p. 5 para 3, p. 13 fig 5.
McNeely et al., "Decreased circulation time offsets increased efficacy of PEGylated noncarriers targeting folate receptors of glioma." Nanotechnology, vol. 18 No. 38 p. 1-11, Sep. 2007, p. 1 right col. para 1, p. 2 right col. para 2, p. 6 right col. para 2.
Edwards K, Johnsson M, Karlsson G, Silvander M. Effect of polyethyleneglycol-phospholipids on aggregate structure in preparations of small unilamellar liposomes. 1997 Biophys. J. 73: 258-266.

(Continued)

*Primary Examiner* — Michael G Hartley
*Assistant Examiner* — Melissa Perreira
(74) *Attorney, Agent, or Firm* — Benjamen E. Kern

(57) ABSTRACT

Compositions and methods are disclosed for evaluating a subject's vasculature integrity, for differentiating between a malignant lesion and a benign lesion, for evaluating the accessibility of a tumor to nano-sized therapeutics, for treating tumors, and for live or real time monitoring of a nano-probe's biodistribution.

23 Claims, 11 Drawing Sheets

OTHER PUBLICATIONS

Mulder WJ, Douma K, Koning GA, Van Zandvoort MA, Lutgens E, Daemen MJ, Nicolay K, Strijkers GJ. Lipsome-enhanced MRI of neointimal lesions in the ApoE-KO mouse. 2006 Magn. Reson. Med. 55: 1170-1174.

Zheng J, Perkins G, Kirilova A, Allen C, Jaffray DA. Multimodal contrast agent for combined computed tomography and magnetic resonance imaging applications. 2006 Invest. Radiol. 41: 339-348.

Written opinion and search report from related PCT Application No. PCT/US09/47228.

Written opinion and search report from related PCT Application No. PCT/US10/27795.

Dunn Fl, Brennan Tj, Nelson Ae, Robertson Gl. The Role of Blood Osmolality and Volume in Regulating Vasopressin Secretion in the Rat. J. Clin. Invest. 1973, 52, 3212-3219.

Schneider T, Sachse A, Leike J, RoBling G, Schmidtgen M, Drechsler M, Brandl M. Surface modification of continuously extruded contrast-carrying liposomes: effect on their physical properties. 1996 Intl J. of Pharm. 132: 9-21.

Awasthi V D, Garcia D, Klipper R, Goins B A, Phillips W T. Neutral and Anionic Liposome-Encapsulated Hemoglobin: Effect of Postinserted Poly(ethylene glycol)—distearoylphosphatidyl-ethanolamine on Distribution and Circulation Kinetics. J. of Pharm. and Experimental Therapeutics (JPET) 309:241-248, 2004.

Mukundan S Jr, Ghaghada Kb, Badea Ct, Kao Cy, Hedlund Lw, Provenzale Jm, Johnson Ga, Chen E, Bellamkonda Rv, Annapragada A. A liposomal nanoscale contrast agent for preclinical CT in mice. AJR Am J Roentgenol. Feb. 2006;186(2):300-7.

Karathanasis E, Chan L, Balusu Sr, D'Orsi Cj, Annapragada Av, Sechopoulos I, Bellamkonda Rv. Multifunctional nanocarriers for mammographic quantification of tumor dosing and prognosis of breast cancer therapy. Biomaterials. Dec. 2008;29(36):4815-22.

Karathanasis E, Suryanarayanan S, Balusu Sr, McNeeley K, Sechopoulos I, Karellas A, Annapragada Av, Bellamkonda Rv. Imaging nanoprobe for prediction of outcome of nanoparticle chemotherapy by using mammography. Radiology. Feb. 2009;250(2):398-406.

Karathanasis E, Chan L, Karumbaiah L, McNeeley K, D'Orsi Cj, Annapragada Av, Sechopoulos I, Bellamkonda Rv. Tumor vascular permeability to a nanoprobe correlates to tumor-specific expression levels of angiogenic markers. PLoS One. Jun. 9, 2009;4(6):e5843.

Samei E, Saunders Rs, Badea Ct, Ghaghada Kb, Hedlund Lw, Qi Y, Yuan H, Bentley Rc, Mukundan S Jr. Micro-CT imaging of breast tumors in rodents using a liposomal, nanoparticle contrast agent. Int J Nanomedicine. 2009;4:277-82.

Karathanasis E, Suryanarayanan S, Balusu Sr, McNeeley K, Sechopoulos I, Karellas A, Annapragada Av, Bellamkonda Rv. Imaging Nanoprobe for Prediction of Outcome of Nanoparticle Chemotherapy by Using Mammography. Radiology. Feb. 2009;250(2):1-9.

* cited by examiner

US 8,357,351 B2

NANO-SCALE CONTRAST AGENTS AND METHODS OF USE

CROSS-REFERENCE TO RELATED APPLICATIONS

This application is a continuation-in-part of U.S. patent application Ser. No. 11/595,808, filed on Nov. 10, 2006, and U.S. patent application Ser. No. 11/568,936, filed on Dec. 27, 2007, both of which are continuations-in-part of U.S. patent application Ser. No. 10/830,190, filed on Apr. 21, 2004. The above-referenced cases are incorporated herein by reference in their entireties.

STATEMENT REGARDING FEDERALLY SPONSORED RESEARCH OR DEVELOPMENT

This invention was made with United States Government support under NSF Grant No. 0401627 and NSF ERC Grant No. EEC9731643, both of which were awarded by the National Science Foundation. The United States Government has certain rights in the invention.

BACKGROUND

In compromised vasculature and microvasculature systems, blood vessels may display increased leakiness through the blood vessel walls. Diseases where vasculature may be compromised may include cancer, stroke, aneurysm, and internal bleeding. The development of compositions and methods to identify leaky vasculature would be beneficial for early detection and for prognosis of such conditions. Currently, no adequate clinical tool exists to transparently and non-invasively identify and characterize leaky and compromised vasculature.

A related need exists for compositions and methods useful for patient specific, customized tumor characterization and therapy. Nano-systems exist for the diagnosis and treatment of many diseases, especially cancer. Nano-systems offer the possibility of multifunctionality and are being actively developed for in vivo imaging, biomolecular profiling of biomarkers, and targeted drug delivery. Such systems offer the potential to enhance the therapeutic index of anti-cancer agents, either by increasing the drug concentration in the tumor site, decreasing the exposure of healthy tissue, or both.

Most solid tumors require a complex microvasculature network for their growth. This blood microvessel network includes a dense immature blood vessel system with a high degree of tortuosity and increased leakiness through the vessel wall. The success of chemotherapeutic nano-agent therapy for solid tumors is dependent, at least in part, on the access that these agents have to tumors via the so-called leaky vasculature of the tumor. The development and effectiveness of the above described nano-systems is currently limited because no adequate clinical tool exists to transparently and non-invasively predetermine whether the blood vessels of the tumor may be amenable to nano-carrier-mediated therapy in an individualized, patient-specific manner—that is, to determine whether the tumor has a leaky vasculature.

Moreover, no adequate clinical tool exists for co-encapsulation of therapeutic or anticancer agents with non-radioactive contrast enhancing agent to allow for direct X-ray visualization of the biodistribution of the therapeutic or anticancer agents in the body of a subject.

SUMMARY

In one embodiment, a method for evaluating a subject's vasculature integrity is provided, the method comprising: introducing a composition into the subject's vasculature, the composition comprising: liposomes, the liposomes encapsulating one or more nonradioactive contrast-enhancing agents, and the liposomes comprising: cholesterol, at least one phospholipid, and at least one phospholipid which is derivatized with a polymer chain, wherein the average diameter of the liposomes is less than 150 nanometers; generating images of the subject's vasculature; and analyzing the images to detect a leak in the subject's vasculature.

In another embodiment, a method for differentiating between a malignant lesion and a benign lesion is provided, the method comprising: introducing a composition into a lesion of interest, the composition comprising: liposomes, a plurality of the liposomes comprising: at least one first lipid or phospholipid; at least one second lipid or phospholipid which is derivatized with one or more polymers; and at least one sterically bulky excipient capable of stabilizing the liposomes, wherein the average diameter of the liposomes is less than 150 nanometers, and wherein a plurality of the liposomes encapsulate at least one nonradioactive contrast enhancing agent; generating images of the lesion of interest; and analyzing the images to determine the extent of accumulation of the composition in the lesion of interest.

In another embodiment, a method for evaluating the accessibility of a tumor to nano-sized therapeutics is provided, the method comprising: introducing a composition into the tumor, the composition comprising: liposomes, each liposome comprising: at least one first lipid or phospholipid; at least one second lipid or phospholipid which is derivatized with one or more polymers; and at least one sterically bulky excipient capable of stabilizing the liposomes, wherein the average diameter of the liposomes is less than 150 nanometers, and wherein each liposome encapsulates at least one nonradioactive contrast enhancing agent; generating images of the tumor; and analyzing the images to determine the extent of accumulation of the composition in the tumor.

In another embodiment, a composition is provided, the composition comprising: liposomes having an average diameter of less than 150 nanometers, the liposomes comprising: a first lipid or phospholipid; a second lipid or phospholipid which is derivatized with a polymer; and a sterically bulky excipient capable of stabilizing the liposomes; wherein the liposomes co-encapsulate a nonradioactive contrast enhancing agent and a bio-active agent.

BRIEF DESCRIPTION OF THE DRAWINGS

The accompanying figures, which are incorporated in and constitute a part of the specification, illustrate various example compositions, methods, results, and so on, and are used merely to illustrate various example embodiments.

DETAILED DESCRIPTION

Figure 1:
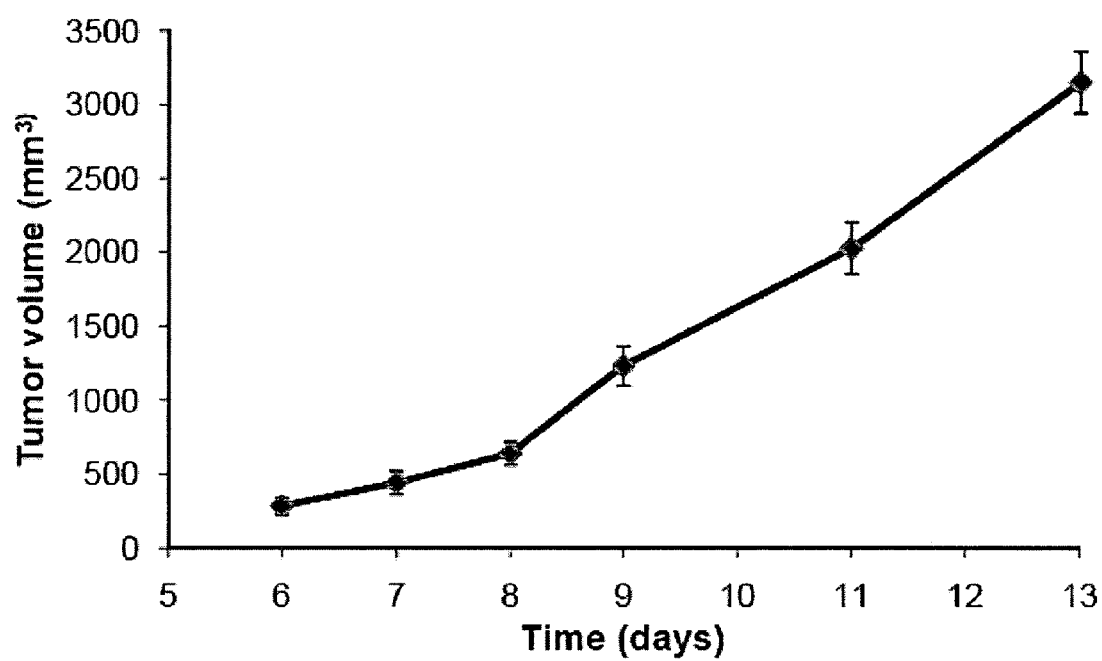
FIG. 1 shows a 13762 MAT B III mammary adenocarcinoma tumor growth curve in Fischer 344 rats.

The design, fabrication, characterization, and application of nano-scale contrast agents (or "nano-probe"(s)) is provided.

A typical nano-probe comprises a liposomal composition comprising a lipid or phospholipid, a stabilizing excipient such as cholesterol, and a polymer-derivatized lipid or phospholipid. Suitable examples of lipids or phospholipids, stabilizing excipients, and polymer-derivatized lipids or phospholipids are set forth in, for example, U.S. patent application Ser. Nos. 10/830,190, 11/595,808, and 11/568,936.

The liposomal compositions typically encapsulate a contrast enhancing agent. Suitable contrast enhancing agents include, for example, non-radioactive iodinated compounds such as iohexol and iodixanol, as described in U.S. patent application Ser. Nos. 10/830,190, 11/595,808, and 11/568,936. The nano-probe may carry high amounts of iodinated contrast agent. For example, the nano-probes may carry as much as 130-200 mg of iodinated compound per mL of liposomal composition. A typical concentration of iodinated compound may be approximately 155 mg/mL.

Other suitable contrast enhancing agents known in the art may be included, as necessary or desirable, to effect imaging by other imaging technologies, such as, for example, ultrasonagraphy, electron beam (EBT), magnetic resonance imaging (MRI), magnetic resonance angiography (MRA), positron emission tomography, and optical imaging, including fluorescence and bioluminescence. For example, in certain embodiments, suitable contrast agents may include fluorescent dyes, such as, for example, fluorescein iso-thiocynate and MRI contrast agents including lanthanide aminocarboxylate complexes such as Gadolinium (III) DTPA and its variants.

The nano-probes are typically about or approximately 100 nm in average diameter, but may range from about 15 to about 150 nm in average diameter. Thus, a suitable liposome average diameter may be less than about 150 nm, less than about 120 nm, and less than about 100 nm. The nano-probes typically have long blood circulation times (e.g., $t_{1/2} \approx 18$ h in rats).

The nano-probes may be prepared, for example, by the methods disclosed in U.S. patent application Ser. Nos. 10/830,190, 11/595,808, and 11/568,936, and in Example 1, below.

Generally speaking, the nano-probe may be detected using at least one of the following X-ray diagnostic techniques: computed topography (CT), micro-CT, mammography, and chest X-ray. In other embodiments, the nano-probe may be imaged using at least one of MRI, magnetic resonance spectroscopy, bioluminescence imaging, ultrasound, optical imaging, and optical spectroscopy.

In one embodiment, a method for evaluating a subject's vasculature integrity is provided. The method, exemplified in Example 2, below, comprises: introducing a composition (a nano-probe) into the subject's vasculature, the composition comprising: liposomes, each liposome encapsulating one or more nonradioactive contrast-enhancing agents, and each liposome comprising: cholesterol, at least one phospholipid, and at least one phospholipid which is derivatized with a polymer chain, wherein the average diameter of the liposomes is less than 150 nanometers; generating X-ray images of the subject's vasculature; and analyzing the X-ray images to detect a leak in the subject's vasculature. According to one embodiment of the method, the nano-probes can interrogate and quantify the extent of blood vessel integrity non-invasively using X-ray based imaging techniques.

In one embodiment of the method, analyzing the X-ray images comprises distinguishing areas having an enhanced X-ray signal from areas having little or no X-ray signal. In another embodiment of the method, the composition is characterized in that the composition accumulates in an extravascular region of the subject's vasculature when a leak exists in the subject's vasculature, in comparison to an intravascular region of the subject's vasculature, thereby achieving enhanced X-ray signal in the extravascular region. In one embodiment of the method, a low nano-probe dose containing a small amount of non-radioactive iodinated compound may achieve X-ray signal enhancement of the extravascular space of a leaky vasculature while the low intravascular levels of the iodinated nano-probe produce little or no signal enhancement.

In another embodiment of the method, generating X-ray images comprises generating X-ray images using at least one of CT, micro-CT, mammography, and chest X-ray.

In one embodiment, the leak is indicative of at least one of cancer, inflammation, stroke, aneurism, wound healing or other reparative processes, and trauma. As such, in one embodiment, the nano-probes may facilitate the detection of injured, leaky blood vessels caused by a variety of diseases such as cancer, inflammation, stroke, aneurism, internal bleeding due to trauma, and angiogenesis due to regenerative processes such as wound healing.

In another embodiment, a method is provided for differentiating between a malignant lesion and a benign lesion. The method comprises: introducing a composition (e.g., a nano-probe) into a lesion of interest, the composition comprising: liposomes, the liposomes comprising: at least one first lipid or phospholipid; at least one second lipid or phospholipid which is derivatized with one or more polymers; and at least one sterically bulky excipient capable of stabilizing the liposomes, wherein the average diameter of the liposomes is less than 150 nanometers, and wherein the liposomes encapsulate at least one nonradioactive contrast enhancing agent. In one embodiment of the method, the composition may be characterized in that the composition accumulates in a malignant lesion to a greater extent than in a benign lesion because malignant tumors have an increased permeability to 5-200 nm sized particles. The method further comprises generating X-ray images of the lesion of interest and analyzing the X-ray images to determine the extent of accumulation of the composition in the lesion of interest.

In another embodiment, a method is provided for evaluating the accessibility of a tumor to nano-sized therapeutics. The method, exemplified in Example 4, below, comprises: introducing a composition (a nano-probe) into a tumor of interest, the composition comprising: liposomes, a plurality of the liposomes comprising: at least one first lipid or phospholipid; at least one second lipid or phospholipid which is derivatized with one or more polymers; and at least one sterically bulky excipient capable of stabilizing the liposomes, wherein the average diameter of the liposomes is less than 150 nanometers, and wherein a plurality of the liposomes encapsulate at least one nonradioactive contrast enhancing agent; generating X-ray images of the tumor; and analyzing the X-ray images to determine the extent of accumulation of the composition in the tumor.

In yet another embodiment, a composition is provided. The composition, an example of which is provided at Example 5, below, may comprise: liposomes having an average diameter of less than 150 nanometers, each liposome comprising: a first lipid or phospholipid; a second lipid or phospholipid which is derivatized with a polymer; and a sterically bulky excipient capable of stabilizing the liposomes; wherein each liposome co-encapsulates a nonradioactive contrast enhancing agent and at least one bio-active agent, including, but not limited to, a chemotherapeutic, a gene, a protein, a small molecule, and a peptide. In one embodiment of the composition, the first lipid or phospholipid comprises 1,2-dipalmitoyl-sn-glycero-3-phosphocholine (DPPC). In another embodiment of the composition, the sterically bulky excipient capable of stabilizing the liposomes comprises cholesterol. In another embodiment of the composition, the second lipid or phospholipid which is derivatized with a polymer comprises 1,2-distearoyl-sn-glycero-3-phosphoethanolamine-N-[methoxy(poly(ethylene glycol))-2000] (mPEG2000-DSPE). In another embodiment of the composition, the first lipid or phospholipid, the second lipid or phospholipid which is derivatized with a polymer, and the sterically bulky excipient capable of stabilizing the liposomes, are present in a ratio of 55:40:5. In another embodiment of the composition, the chemotherapeutic comprises doxorubicin. In another embodiment of the composition, the liposomes have an average diameter of about 100 nm.

In one embodiment, the composition may allow for live or real time monitoring of the nano-probe biodistribution, thereby allowing for patient-specific therapies. In another embodiment, non-invasive pharmacokinetics of a therapeutic agent may be achieved when the therapeutic agent is co-encapsulated with contrast agent within the nano-probe as described with respect to the composition. In another embodiment, the nano-probe is further multi-functional in that the nano-probe may be actively targeted via antibodies and peptides.

One example therapeutic that may be suitable for co-encapsulation is anthracyclines. Liposomal anthracyclines have been developed to increase the therapeutic index of the anthracycline by maintaining antitumor efficacy while improving the safety profile. Anthracyclines, including doxorubicin, are among the most potent chemotherapeutic agents. However, this family of chemotherapeutics exemplifies the limitation of many potent anticancer drugs in that they are limited by highly problematic system toxicities, which result in myelosuppression, acute nausea and vomiting, stomatitis, and cardiotoxicity. Polyethylene glycol-coated (PEGylated) liposomal doxorubicin, a 100 nm lipid sac with a long blood circulation ($t_{1/2} \cong 55$ h), has been approved in the United States for clinical use for treatment of refractory Kaposi's sarcoma and ovarian cancer. PEGylated liposomal doxorubicin has also been investigated for breast cancer therapy, and has shown similar efficacy and significantly lower cardiotoxicity when compared to conventional doxorubicin. Many other drugs loaded into liposomes are approved or undergoing clinical evaluation for cancer therapy, and may be suitable for co-encapsulation as described herein, including, but not limited to, vincristine, lurtotecan, all-trans retinoic acid, platinum compounds, annamycin, and DNA plasmid encoding HLA-B7 and $\beta 2$ microglobulin.

In certain embodiments, suitable imaging techniques for the detecting the composition may include, for example, at least one of the following X-ray diagnostic techniques: computed topography (CT), micro-CT, mammography, and chest X-ray. In other embodiments, the nano-probe may be imaged or detected using at least one of MRI, ultrasound, and optical imaging, including fluorescence or bioluminescence imaging.

EXAMPLES

Example 1

Preparation and Characterization of an Example Nano-Probe

A highly concentrated iodine solution (600 mgI/mL) was prepared by dissolving iodixanol powder (lyophilized from Visapaque 320, GE Healthcare) in ultrapure water under continuous stirring and heating at 70° C. A lipid solution in ethanol comprising 1,2-dipalmitoyl-sn-glycero-3-phosphocholine (DPPC), cholesterol, and 1,2-distearoyl-sn-glycero-3-phosphoethanolamine-N-[methoxy(poly(ethylene glycol))-2000] (mPEG2000-DSPE) in the molar ratio 55:40:5 was hydrated with the iodine solution at 70° C., followed by sequential extrusion on a Lipex Thermoline extruder (Northern Lipids, Vancouver, Canada). This resulted in encapsulation of the iodine solution within the central aqueous core of polyethylene glycol-stabilized (PEGylated) liposomes. Free, un-encapsulated iodixanol was replaced by a saline solution (300 mM NaCl) with the same osmolarity as the internal iodinated phase of the liposome using a two day dialysis against 300 mM NaCl using a 100,000 MWCO dialysis tubing. Following concentration via diafiltration using MicroKros modules (Spectrum Laboratories, California) with a 50 nm cutoff pore size, the liposomal iodine and lipid content were measured to be 155 mg/mL (all encapsulated) and 165 mM, respectively. The average diameter of the liposomes was 96 nm (sd=8 nm) as determined by dynamic light scattering. The 596 mOsm/kg water osmolality of the formulation allowed intravenous injection, since the liposomal walls can sustain the osmotic pressures expected to occur in isotonic environments. Indeed, in vitro leakage experiments against isotonic phosphate buffered saline exhibited negligible leakage of the encapsulated iodine (less than 5% of the initial payload) over the period of three days.

Example 2

Imaging Study Using Nano-Probe of Example 1

The nano-probe of Example 1 was tested in a rat breast tumor model developed by inoculation of mammary adenocarcinoma cells (13762 MAT B III from ATCC) into the right flank of Fischer female rats. The imaging studies started on day seven after tumor inoculation (tumor volume approximately 440 mm$^3$; see FIG. 1 for tumor growth curve). Tumor volumes (n=15) were obtained by caliper measurements.

Contrast-enhanced mammography was performed with a commercial digital mammography system (Senographe 2000D, GE Healthcare) at 49 kVp and 63 mAs with a rhodium target and an extra copper filter of 0.3 mm thickness. These settings were used to shape the x-rays to have optimal energies for iodine. Under these conditions, an optimal X-ray spectrum was obtained containing the largest number of X-rays with energies above the k-edge of iodine while X-ray dose was significantly reduced when compared to standard mammography. Initial studies were performed with high doses of the nano-probe to obtain a vascular image. A pre-contrast image (FIG. 2(a)) and post-contrast images were acquired 1, 5, 10, and 15 minutes after tail vein injection of the nano-probe. Blood vessels were clearly visible (FIG. 2(b)) at a 1,300 mgI/kg body weight dose of the nano-probe achieving blood concentrations of 20 mgI/mL. In the case of an adult human, this would correspond to a dose of about 654 mL of the nano-probe (assuming a blood volume of five liters), which is prohibitively large for use in humans. However, this high dose was used to clearly visualize the blood vessels that the mammography system was capable of detecting.

Figure 2:
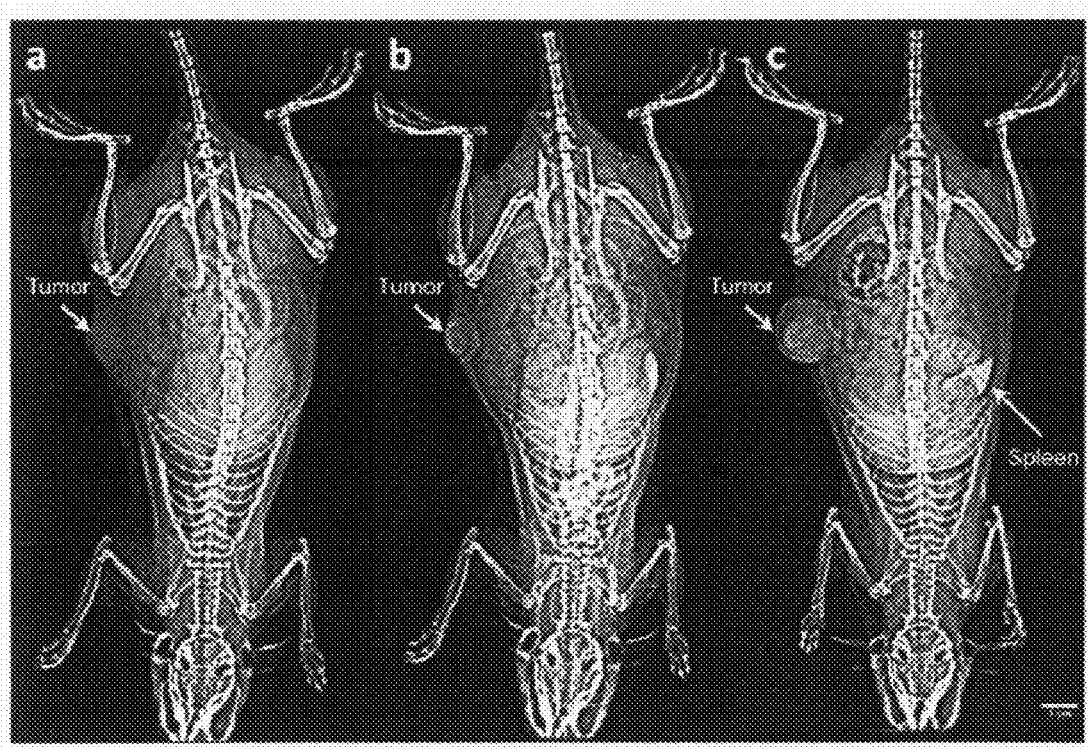
FIG. 2 shows whole body images of a rat with a breast tumor in its right flank obtained using a clinical digital mammography system before (a) and 1 minute after administration of a "high" dose (1,244 mgI/kg) of an example nano-probe (b) resulting in vasculature visualization of the tumor site as well as normal tissues. A 72-hour post-contrast image of a different rat injected with a "low" does (455 mgI/kg) of the example nano-probe (c) reveals the accumulation of the nano-probe in the tumor and the spleen, while the vasculature is not visible.

In monitoring the fate of the nano-probe studies, a pre-contrast image (indicated as t=0) and post-contrast images were obtained 24, 72, and 120 hours after administration of the nano-probe at a dose of 455 mgI/kg body weight. This corresponds to 195 mg lipid/kg body weight, which is about two times higher than the highest lipid dose of liposomal drugs when employed in clinical practice. FIG. 2(c) shows an image of an animal obtained 72 h after the nano-probe injection. No blood vessels are visible in the normal tissue (as compared to the enhanced vasculature observed in FIG. 2(b)), while the spleen and the tumor were enhanced. The spleen enhancement was expected since liposomes within the extravascular space of the tumor provided for the detection of the nano-probe (when maximum iodine in the blood circulation was expected), since the iodine levels in the blood were below the detectable threshold.

Figure 3:
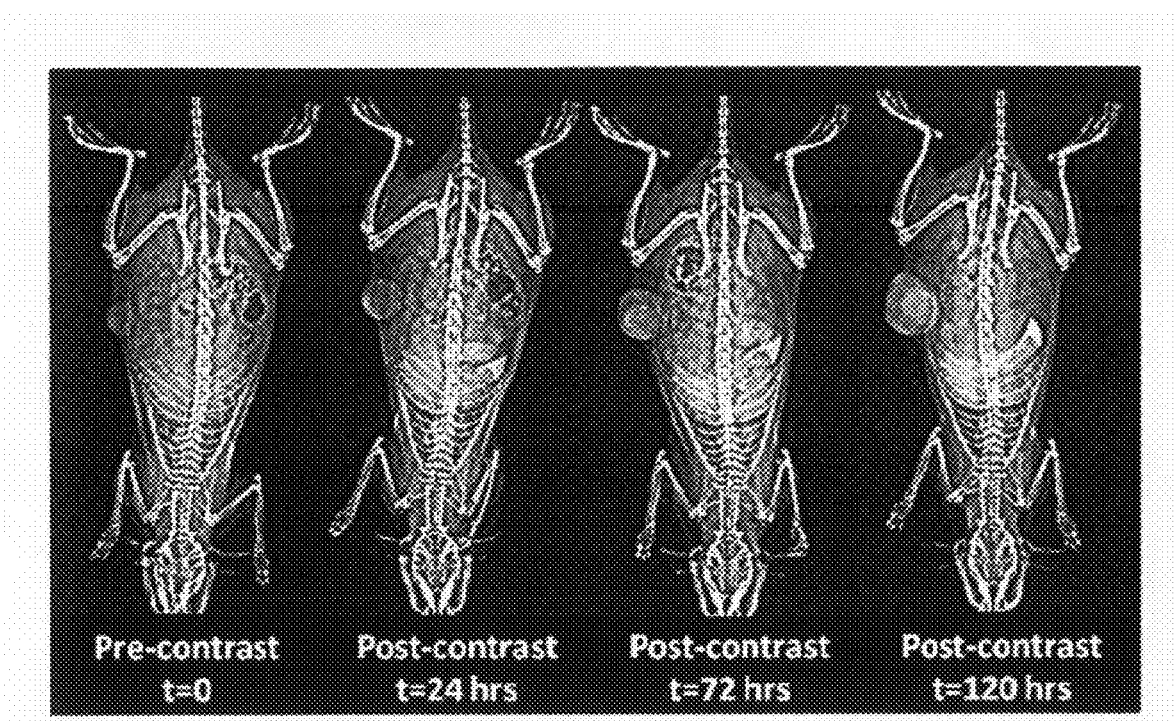
FIG. 3 shows whole body images of a rat (rat 3 as indicated in FIG. 4) obtained using a clinical digital mammography system before and 24, 72, and 120 hours after administration of a "low" dose (455 mgI/kg) of the example nano-probe.
Figure 4:
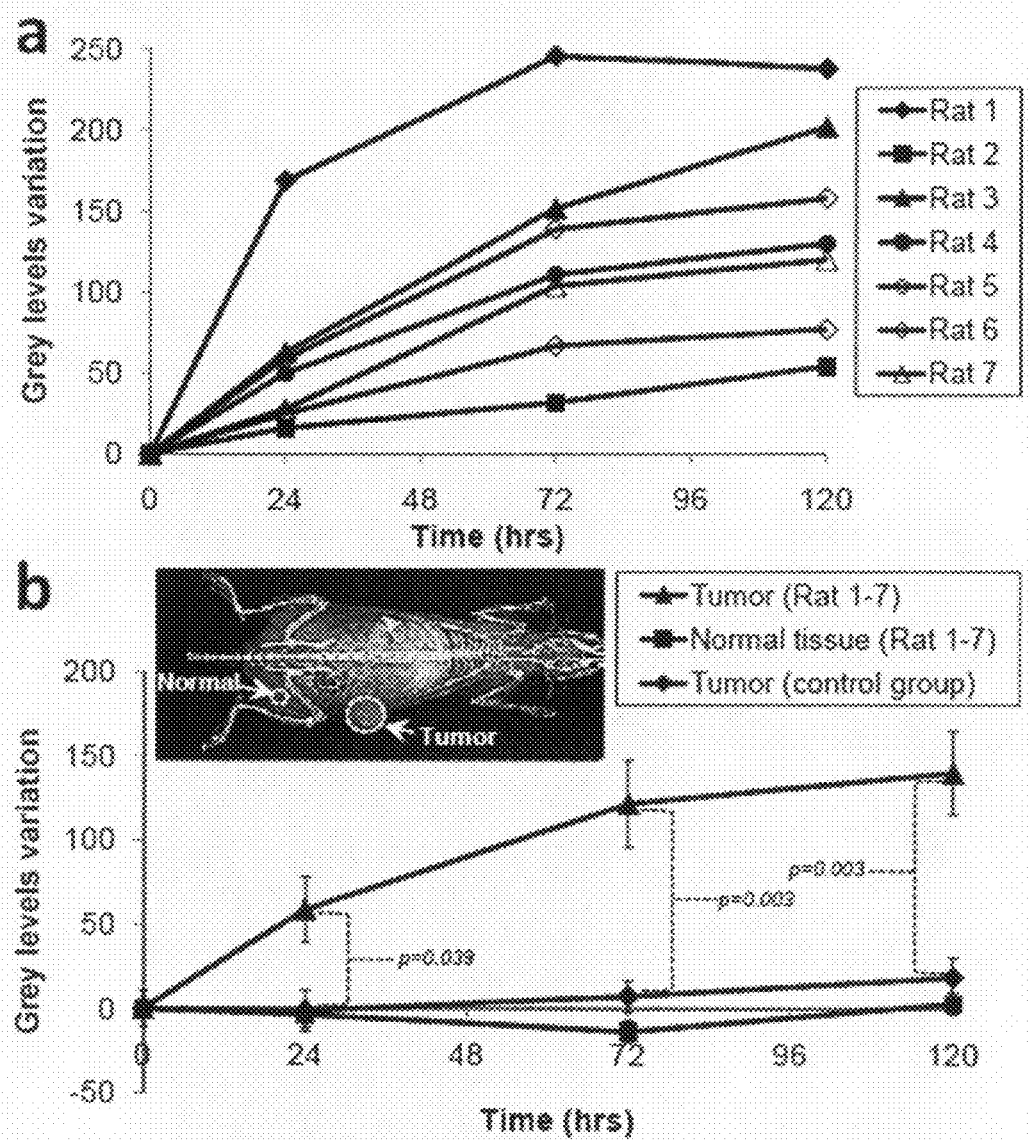
FIG. 4 shows a comparison of (a) the uptake of the example nano-probe by the breast tumor of seven rats over five days as imaged by a clinical mammography system; and (b) the uptake of the example nano-probe by the normal tissue of the same seven rats over the same time frame.

FIG. 3 displays the timeline of the nano-probe accumulation within the tumor lesion for a period of five days. In the same manner, a group of animals (n=7) was imaged and monitored at the post-contrast defined time points exhibiting a similar behavior. FIG. 4(a) summarizes the time course of the tumor enhancement by quantifying the grey levels of the lesions using ImageJ software (NIH, Bethesda, Md.). A normalized tumor enhancement was calculated by subtracting each post-contrast value (t>0) from its tumors that showed a slow gradual increase of the enhancement during the 120 h time course (indicated as rat 2 and 6 in FIG. 4(a)), whereas other tumors displayed a faster increase (indicated as rat 3, 4, and 5 in FIG. 4(a)). Another tumor exhibited an initial rapid enhancement at t=24 h followed by a plateau. At t=120 h, there were lesions with low enhancement and other lesions with much higher enhancement. This discrepancy suggests that different amounts of the nano-probe leaked into each tumor.

Figure 5:
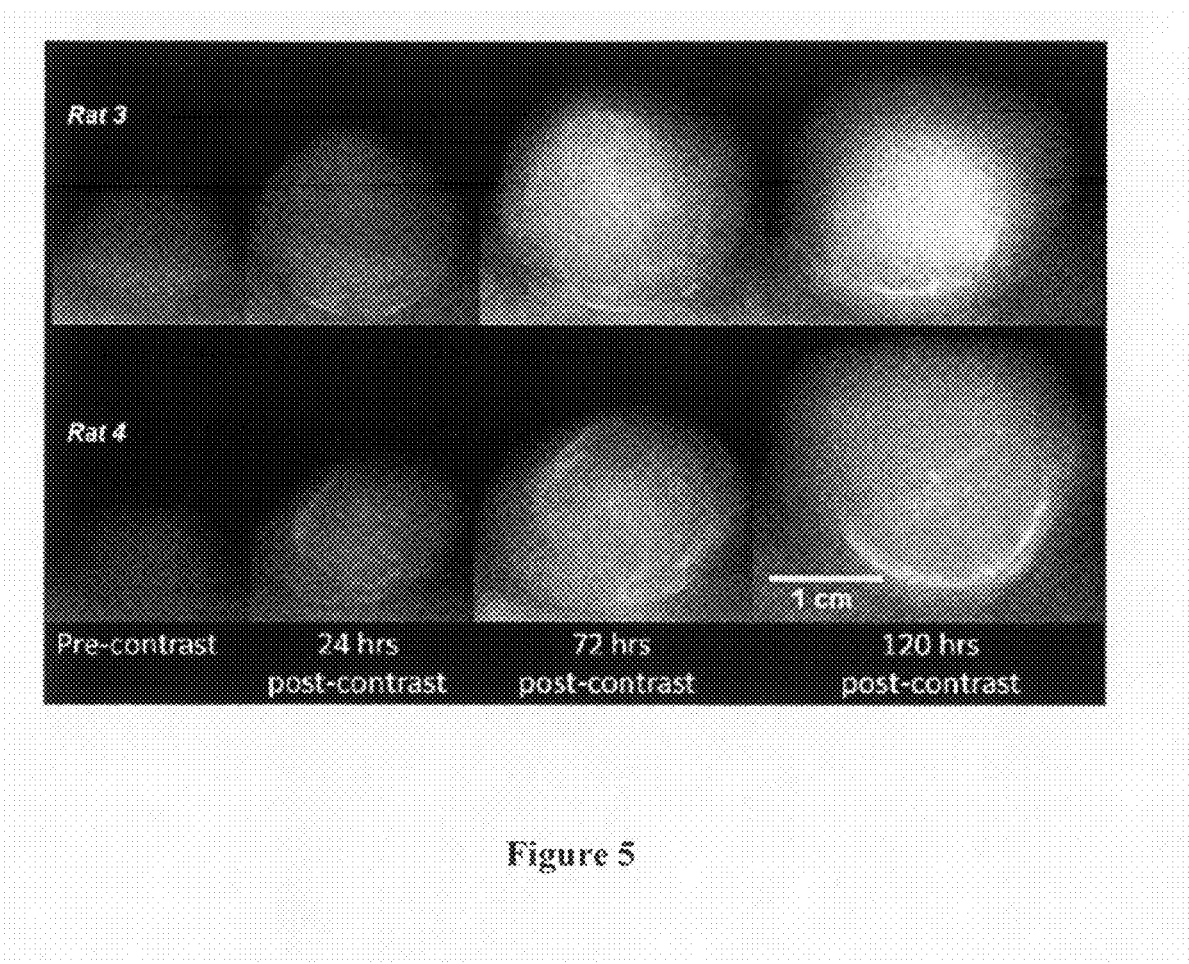
FIG. 5 shows an example of mammography images of a breast tumor with high uptake of the example nano-probe (rat 3) and a breast tumor with moderate uptake of the example nano-probe (rat 4) over a five day time period.

The pattern of tumor enhancement due to the nano-probe was plotted in FIG. 4(b) and compared against the normal tissue of the animals in the same group or the tumor site of a control group (injected with no agent) exhibiting statistical differences. No enhancement was observed in normal tissues, suggesting that the nano-probe levels in the blood were below the detectable threshold of the mammography, and implying that no endogenous changes of the tumor tissue could contribute such a significant enhancement as the one seen in the case of the non-probed lesions. Examples of mammography images of a tumor lesion with high uptake and a tumor lesion with moderate uptake are shown in FIG. 5.

Example 3

Comparative Examples (control groups)

Figure 6:
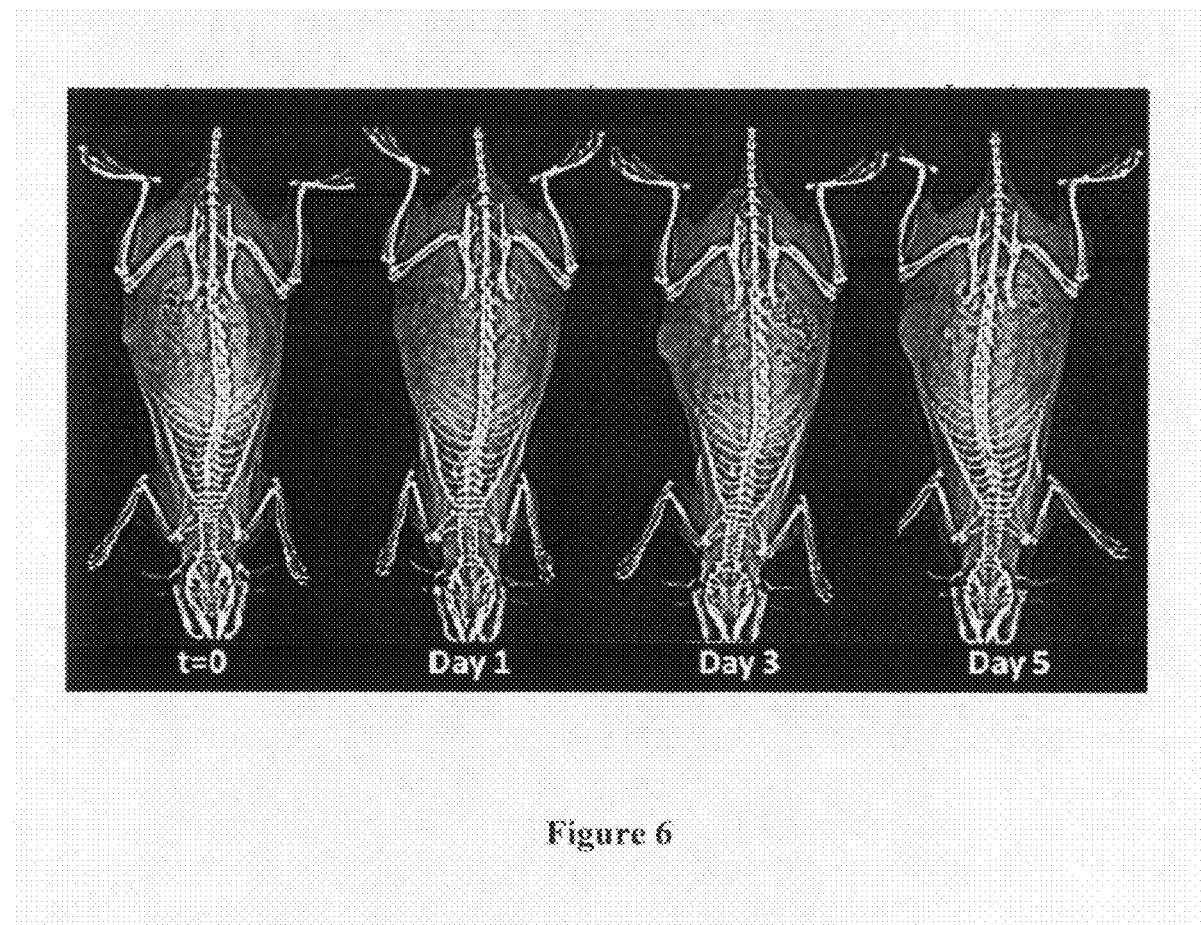
FIG. 6 shows whole body images of a rat obtained using a clinical digital mammography system injected with saline of equal volume of the volume with the example nano-probe. The time points coincide with pre- and post-contrast images of the nano-probed rats.
Figure 7:
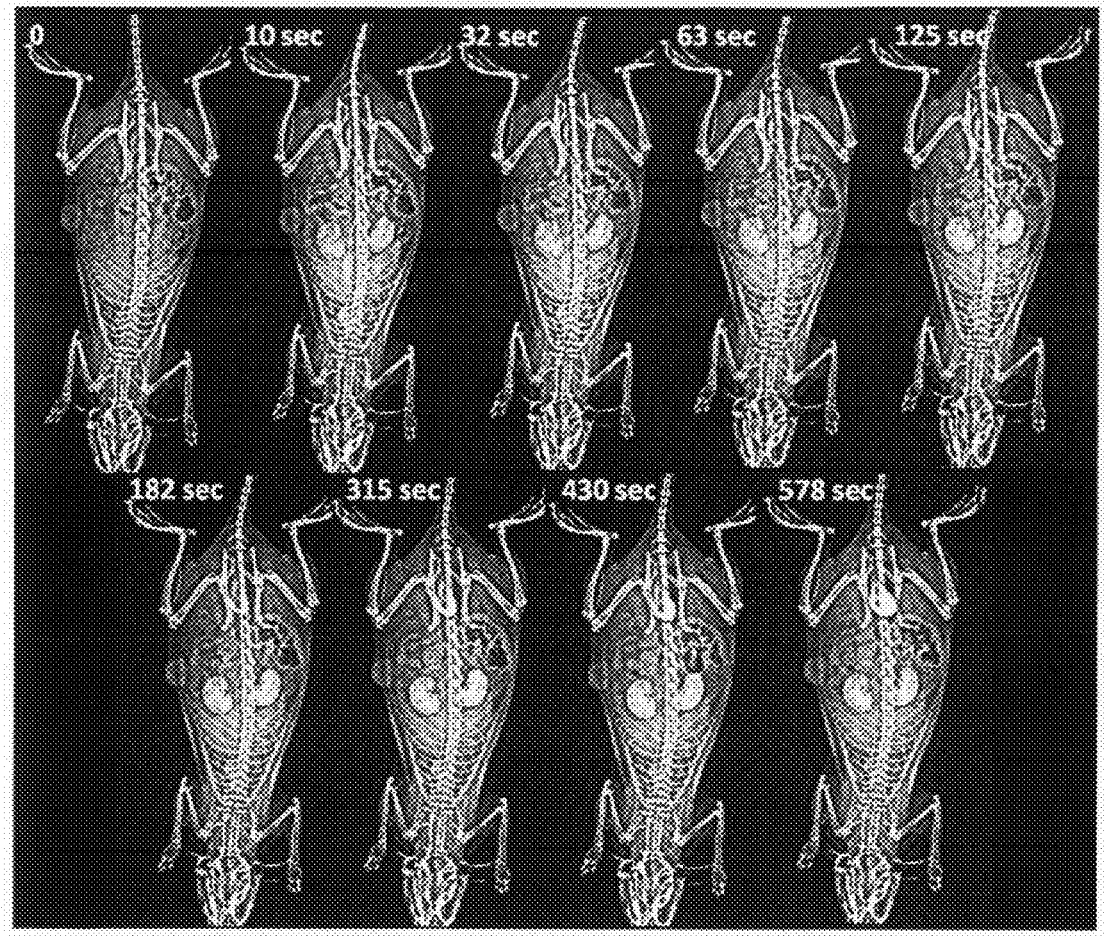
FIG. 7 shows whole body images of a rat obtained using a clinical digital mammography system before and 10, 32, 63, 125, 182, 315, 430, and 578 seconds after administration with a "high" dose (1,344 mgI/kg) of a conventional contrast agent (iohexol).
Figure 8:
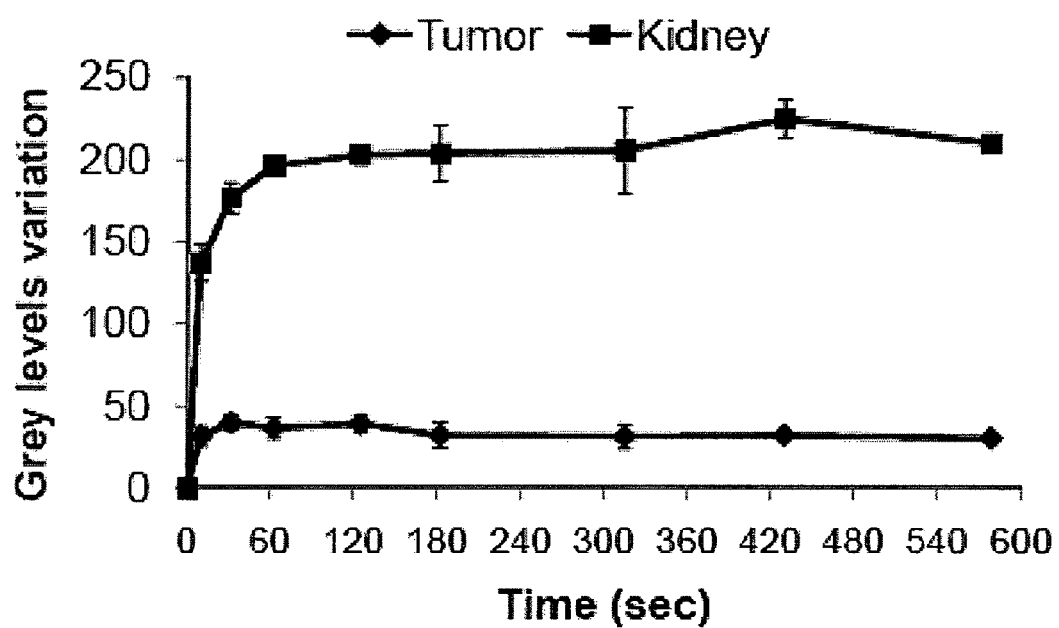
FIG. 8 shows example results of the administration of a high dose (1,344 mgI/kg) of a conventional contrast agent (iohexol) to a rat, which exhibited negligible tumor enhancement due to rapid renal clearance.

Whole body mammograms of a rat injected with no contrast agent (control group) is shown in FIG. 6. Another control group was injected with a conventional iodinated agent (iohexol) at an iodine dose equivalent to the high dose of 1,344 mgI/mL of the nano-probe. (See FIG. 7). Within the first minute after injection, the normal vasculature and the tumor lesion exhibited a slight enhancement, but the iodinated agent was rapidly cleared via the kidneys. (See FIG. 8).

Example 4

Non-Invasive Prediction of Nano-Chemotherapy Success

Figure 9:
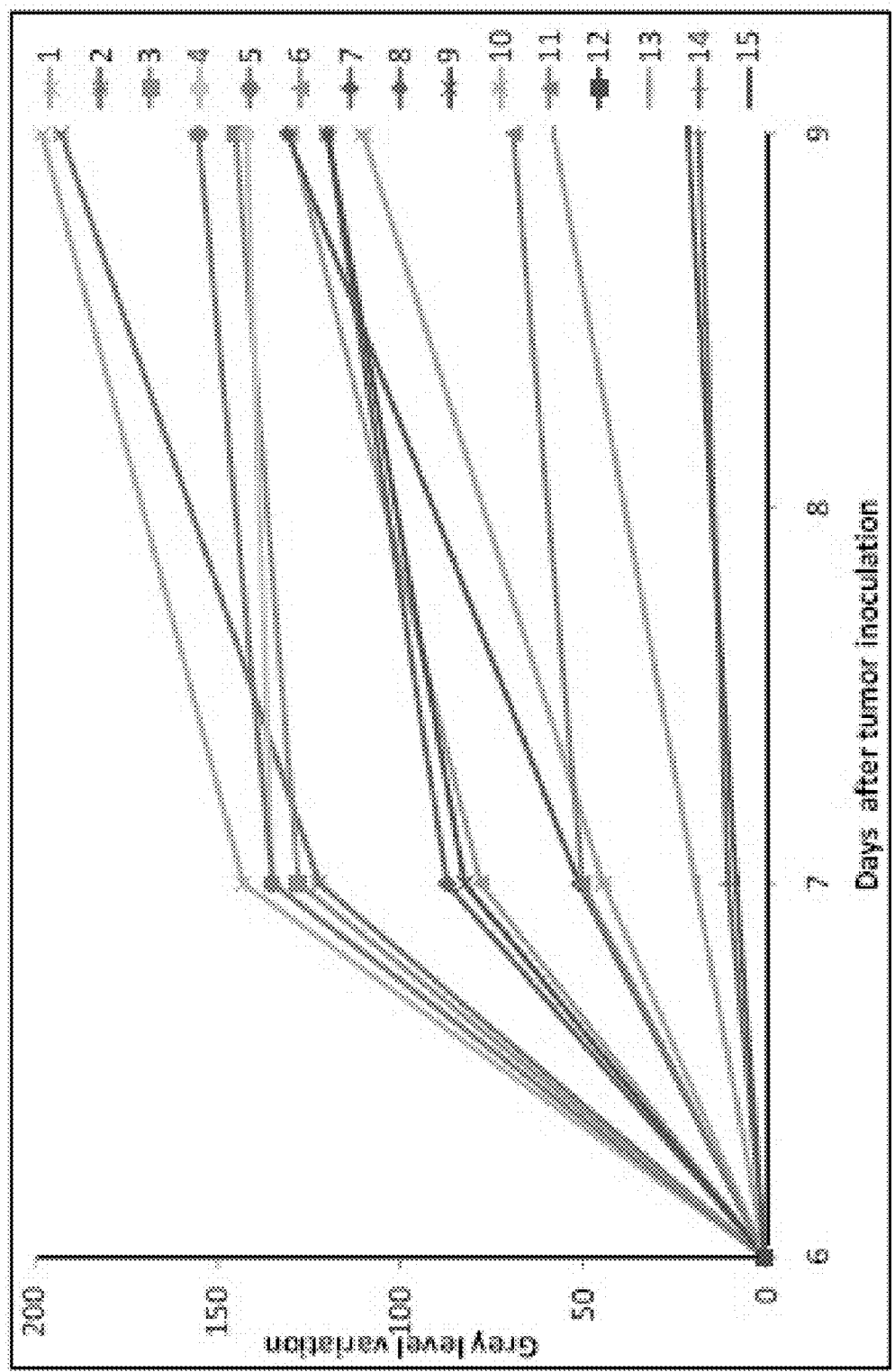
FIG. 9 shows a comparison of the uptake of the example nano-probe by the breast tumor of 15 rats within the period of three days as imaged by a clinical mammography system.

The prediction accuracy of the nano-probe was tested in a rat breast tumor model developed by inoculation of mammary adenocarcinoma cells (13762 MAT B III from ATCC) into the right flank of Fischer female rats. The imaging studies started on day six after tumor inoculation. Contrast-enhanced mammography was performed with a commercial digital mammography system (Senographe 2000D, GE Healthcare) at 49 kVp and 63 mAs with a rhodium target and an extra copper filter of 0.3 mm thickness. The animals (n=15) were injected with the example nano-probe in an amount of 455 mgI/kg b.w. FIG. 9 summarizes the time course of the tumor enhancement by quantifying the grey levels of the lesions using ImageJ software (t>0) from its pre-contrast value (t=0). It is observed that the enhancement profiles exhibit dissimilar patterns. Immediately after the imaging session (at day 9 after tumor inoculation), the animals were injected with liposomal doxorubicin at a dose of 10 mg doxorubicin per kg b.w.

Figure 10:
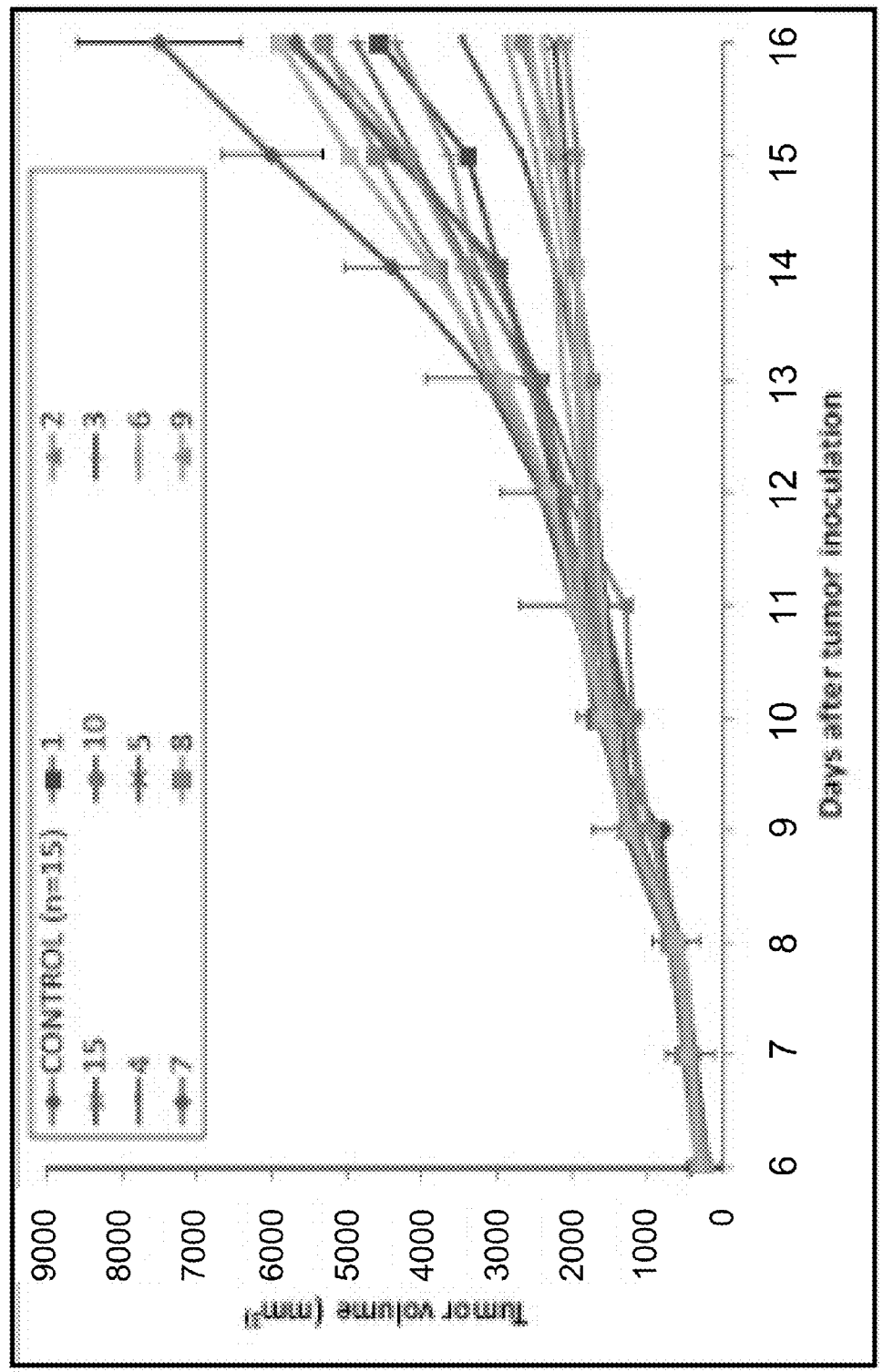
FIG. 10 shows tumor growth curves of a control (untreated) group and group treated with liposomal doxorubicin.

The response of the tumor to the drug was evaluated by measuring the size of the tumor using a caliper. FIG. 10 summarizes the tumor growth curves of all of the animals obtained by caliper measurements. The growth curves exhibit high variability, implying that each tumor responded differently to the chemotherapeutic. The animals that displayed higher uptake of the nano-probe responded better to the treatment (smaller tumor volumes).

Figure 11:
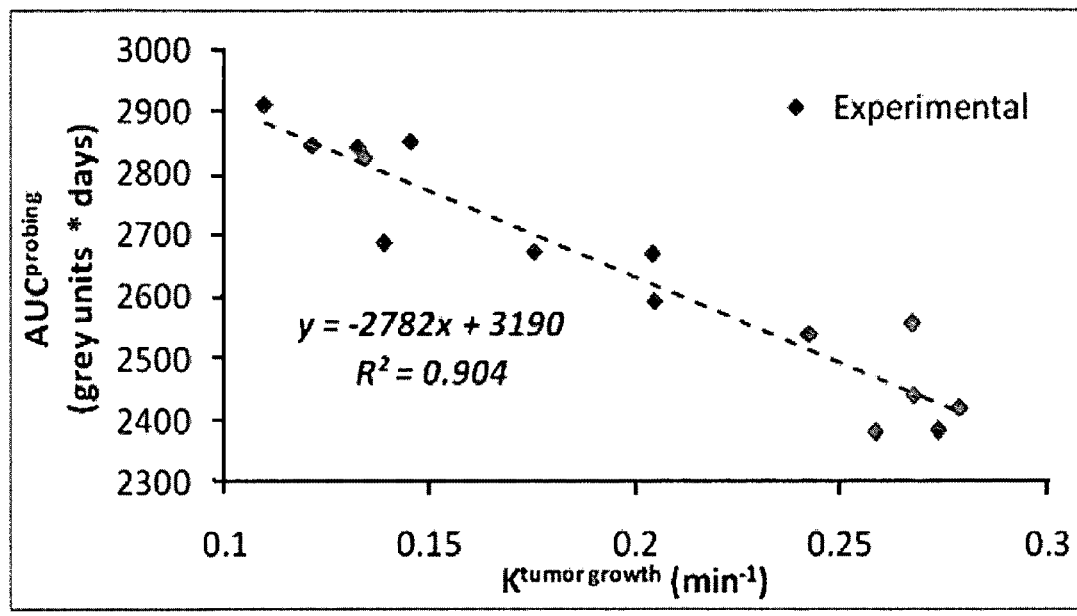
FIG. 11 shows tumor growth curves of a control (untreated) group and group treated with liposomal doxorubicin.

To quantify the relation of the nano-probe prediction to the therapy response, the tumor growth curves (FIG. 10) were fitted to mono-exponential functions (i.e., $dV/dt = K^{tumor\ growth} * t$, where V is tumor volume) to calculate the growth rate constant, $K^{tumor\ growth}$. The Area Under the Curve ($AUC^{probing}$) of the nano-probe uptake profiles were calculated from FIG. 9. The $K^{tumor\ growth}$ of each animal was plotted against the $AUC^{probing}$ of each animal in FIG. 11. High $AUC^{probing}$ means high intratumoral accumulation of the nano-probe predicting high success of the nano-chemotherapeutic, whereas low $K^{tumor\ growth}$ means slow tumor growth or good response to the treatment.

Example 5

Preparation and in vitro Characterization of an Example Nano-scale Liposome Co-Encapsulating Contrast Agent and Chemotherapeutic A lipid solution in ethanol comprising DPPC, cholesterol, and mPEG(2000)-DSPE in the molar ratio 55:40:5 was hydrated with a 300 mM ammonium sulfate iodinated solution (iohexol; 350 mgI/mL) at 70° C. followed by sequential extrusion on a Lipex Thermoline extruder (Northern Lipids, Vancouver, Canada). This resulted in encapsulation of the iodine solution within the central aqueous core of PEGylated liposomes. Free, unencapsulated iodixanol was removed from the external phase of the liposome using a two day dialysis against 300 mM ammonium sulfate using a 100,000 MWCO dialysis tubing. The liposomes were then dialyzed for 12 h with a 100 kDa MWCO dialysis tubing against a phosphate-buffered saline (PBS) solution to establish an ammonium sulfate gradient for doxorubicin loading.

The liposomal formulation was actively loaded with doxorubicin by an ammonium sulfate gradient. Briefly, liposomes and doxorubicin were mixed at a ratio of 0.1 mg of doxorubicin per 1 mg of DPPC in the liposomes. The liposome-doxorubicin suspension was heated at 35° C. for 25 min. The liposomes were left overnight at room temperature and dialyzed twice in 100 kDa MWCO membrane against PBS to remove unencapsulated doxorubicin. Following concentration, via diafiltration, using MicroKros modules (Spectrum Laboratories, California) with a 50 nm cutoff pore size, the liposomal iodine and doxorubicin content was measured to be 91 mg/mL and 1.2 mg/mL (all encapsulated), respectively. The average diameter of the liposomes was 102 nm (sd=6 nm) as determined by dynamic light scattering.

It is, of course, not possible to describe every conceivable combination of components or methodologies for purposes of describing the compositions, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicants' general inventive concept. A person of ordinary skill will readily recognize that optimizing or manipulating any one of these variables may or will require or make possible the manipulation of one or more of the other of these variables, and that any such optimization or manipulation is within the spirit and scope of the present embodiments.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. It should be noted that the term "about" may mean up to and including ±10% of the stated value. For example, "about 10" may mean from 9 to 11.

Furthermore, while the compositions, methods, and so on have been illustrated by describing examples, and while the examples have been described in considerable detail, it is not the intention of the applicant to restrict, or in any way, limit the scope of the appended claims to such detail. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A method for evaluating a subject's vasculature integrity, the method comprising:
    introducing a composition into the subject's vasculature, the composition comprising: liposomes, the liposomes encapsulating one or more iodinated nonradioactive contrast enhancing agents, and the liposomes comprising: cholesterol, at least one phospholipid, and at least one phospholipid which is derivatized with a polymer chain, wherein the average diameter of the liposomes is less than 150 nanometers;
    generating images of the subject's vasculature; and
    analyzing the images to detect a leak in the subject's vasculature.

2. The method of claim 1, wherein the generating images comprises generating X-ray images.

3. The method of claim 1, wherein the generating images comprises generating images before and after introducing the composition into the subject's vasculature.

4. The method of claim 1, wherein the analyzing the images comprises distinguishing areas having an enhanced signal from areas having little or no signal.

5. The method of claim 1, wherein the composition is characterized in that the composition accumulates in an extravascular region of the subject's vasculature when a leak exists in the subject's vasculature, in comparison to an intravascular region of the subject's vasculature, thereby enhancing the signal in the extravascular region.

6. The method of claim 2, wherein the generating X-ray images comprises generating X-ray images using at least one of computed tomography, micro-computed tomography, mammography, and chest X-ray.

7. The method of claim 1, wherein the generating images comprises generating images using at least one of MRI, ultrasound, and optical imaging, including fluorescence or bioluminescence imaging.

8. The method of claim 1, wherein the leak is indicative of at least one of cancer, stroke, aneurism, healing, and trauma.

9. A method for differentiating between a malignant lesion and a benign lesion, the method comprising:
    introducing a composition into a lesion of interest, the composition comprising:
        liposomes, the liposomes comprising:
            at least one first lipid or phospholipid;
            at least one second lipid or phospholipid which is derivatized with one or more polymers;
            at least one sterically bulky excipient capable of stabilizing the liposomes, wherein the average diameter of the liposomes is less than 150 nanometers, and wherein the liposomes encapsulate at least one iodinated nonradioactive contrast enhancing agent;
    generating images of the lesion of interest; and
    analyzing the images to determine the extent of accumulation of the composition in the lesion of interest.

10. The method of claim 9, wherein the composition is characterized in that the composition accumulates in a malignant lesion to a greater extent than in a benign lesion.

11. The method of claim 9, wherein the generating images comprises generating X-ray images.

12. A method for evaluating the accessibility of a tumor to nano-sized therapeutics, the method comprising:
introducing a composition into the tumor, the composition comprising: liposomes, the liposomes comprising: at least one first lipid or phospholipid; at least one second lipid or phospholipid which is derivatized with one or more polymers; and at least one sterically bulky excipient capable of stabilizing the liposomes, wherein the average diameter of the liposomes is less than 150 nanometers, and wherein the liposomes encapsulate at least one iodinated nonradioactive contrast enhancing agent;
generating images of the tumor; and
analyzing the images to determine the extent of accumulation of the composition in the tumor.

13. The method of claim 12, wherein the generating images comprises generating X-ray images.

14. A method for treating a tumor and monitoring the treatment, comprising:
introducing a composition into the tumor, the composition comprising:
liposomes, the liposomes comprising:
at least one first lipid or phospholipid;
at least one second lipid or phospholipid which is derivatized with one or more polymers; and
cholesterol,
wherein the liposomes co-encapsulate:
at least one iodinated nonradioactive contrast enhancing agent; and
at least one bioactive agent,
and wherein the average diameter of the liposomes is less than 150 nanometers; and
generating X-ray images of the tumor.

15. The method of claim 14, wherein the tumor is a cancerous tumor.

16. The method of claim 14, wherein the at least one first lipid or phospholipid comprises 1,2-dipalmitoyl-sn-glycero-3-phosphocholine (DPPC).

17. The method of claim 14, wherein the at least one second lipid or phospholipid which is derivatized with one or more polymers comprises N-carbamylmethoxypoly(ethylene glycol)-1,2-distearoyl-sn-glycerol-3-phosphoethanolamine (mPEG(2000)-DSPE).

18. The method of claim 14, wherein the at least one iodinated nonradioactive contrast enhancing agent comprises at least one of iodixanol and iohexol.

19. The method of claim 14, wherein the at least one bioactive agent comprises a chemotherapeutic agent.

20. The method of claim 14, wherein the at least one bioactive agent comprises doxorubicin.

21. The method of claim 14, wherein the tumor is a cancerous tumor, and wherein:
the at least one first lipid or phospholipid comprises 1,2-dipalmitoyl-sn-glycero-3-phosphocholine (DPPC);
the at least one second lipid or phospholipid which is derivatized with one or more polymers comprises N-carbamylmethoxypoly(ethylene glycol)-1,2-distearoyl-sn-glycerol-3-phosphoethanolamine (mPEG(2000)-DSPE),
wherein the DPPC, the cholesterol, and the mPEG(2000)-DSPE are present in a molar ratio of approximately 55:40:5,
wherein the at least one iodinated nonradioactive contrast enhancing agent comprises at least one of iodixanol and iohexol,
and wherein the at least one bioactive agent comprises doxorubicin.

22. The method of claim 14, wherein the average diameter of the liposomes is about 100 nanometers.

23. The method of claim 14, wherein the encapsulated liposomal iodine is about 91 mg/mL and the bioactive agent content is about 1.2 mg/mL.

* * * * *